US009708377B2

(12) United States Patent
Norton et al.

(10) Patent No.: US 9,708,377 B2
(45) Date of Patent: Jul. 18, 2017

(54) SCORPION TOXIN ANALOGUE AND METHOD FOR TREATING AUTOIMMUNE DISEASES

(71) Applicants: MONASH UNIVERSITY, Victoria (AU); PEPTIDES INTERNATIONAL, INC., Louisville, KY (US); BAYLOR COLLEGE OF MEDICINE, Houston, TX (US)

(72) Inventors: Raymond S. Norton, Victoria (AU); Serdar Kuyucak, New South Wales (AU); M Harunur Rashid, New South Wales (AU); Michael Pennington, Shelbyville, KY (US); Christine Beeton, Pearland, TX (US)

(73) Assignees: Monash University, Victoria (AU); Baylor College of Medicine, Houston, TX (US); Peptides International, Inc., Louisville, KY (US)

( * ) Notice: Subject to any disclaimer, the term of this patent is extended or adjusted under 35 U.S.C. 154(b) by 0 days.

(21) Appl. No.: 15/032,454

(22) PCT Filed: Oct. 28, 2013

(86) PCT No.: PCT/AU2013/001249
§ 371 (c)(1),
(2) Date: Apr. 27, 2016

(87) PCT Pub. No.: WO2015/061826
PCT Pub. Date: May 7, 2015

(65) Prior Publication Data
US 2016/0264634 A1    Sep. 15, 2016

(51) Int. Cl.
*A61K 49/00* (2006.01)
*A61K 39/00* (2006.01)
*A61K 35/12* (2015.01)
*C07K 14/435* (2006.01)
*A61K 38/00* (2006.01)

(52) U.S. Cl.
CPC ........ *C07K 14/43522* (2013.01); *A61K 39/00* (2013.01); *A61K 38/00* (2013.01)

(58) Field of Classification Search
CPC .................................................. A61K 39/00
USPC ............ 424/9.1, 9.2, 184.1, 185.1, 520, 538
See application file for complete search history.

(56) References Cited

U.S. PATENT DOCUMENTS

| | | | |
|---|---|---|---|
| 6,689,749 B1 | 2/2004 | Lebrun et al. | |
| 7,829,666 B2 | 11/2010 | Sabatier et al. | |
| 7,833,979 B2 * | 11/2010 | Sullivan | A61K 47/48215 514/9.7 |
| 2009/0291885 A1 | 11/2009 | Sullivan et al. | |

FOREIGN PATENT DOCUMENTS

| | | |
|---|---|---|
| WO | WO 03-029277 A2 | 4/2003 |
| WO | WO 2010/108154 | 9/2010 |

OTHER PUBLICATIONS

LeBrun, B., et al., Biochem. J., vol. 328, pp. 321-327, 1997.*
International Search Report and Written Opinion prepared by the Korean Intellectual Property Office on Jul. 24, 2014, for International Application No. PCT/AU2013/001249.
Carrega et al., "The impact of the fourth disulfide bridge in scorpion toxins of the alpha-KTx6 subfamily", Proteins, Dec. 1, 2005, vol. 61, No. 4, pp. 1010-1023.
Kim et al., "Peptide Amidation: Production of Peptide Hormones in vivo and in vitro", Biotechnol. Bioprocess Eng. 2001, vol. 6, No. 4, pp. 244-251.
Lebrun et al., "A four-disulphide-bridged toxin, with high affinity towards voltage-gated K+ channels, isolated from *Heterometrus spinnifer* (Scorpionidae) venom", Biochem. J. (1997) 328, pp. 321-327.
Regaya et al., "Evidence for Domain-specific Recognition of SK and KV Channels by MTX and HsTx1 Scorpion Toxins", The Journal of Biological Chemistry, vol. 279, No. 53, Issue of Dec. 31, 2004, pp. 55690-55696.
Savarin et al., Structural and functional consequences of the presence of a fourth disulfide bridge in the scorpion short toxins: Solution structure of the potassium channel inhibitor HsTX1, Protein Science (1999), 8:2672-2685.

* cited by examiner

*Primary Examiner* — Rodney P Swartz
(74) *Attorney, Agent, or Firm* — Sheridan Ross P.C.

(57) ABSTRACT

A novel peptide analogue of the *Heterometrus spinnifer* toxin HsTX1 is disclosed along with its application as, for example, a therapeutic agent for treating an autoimmune disease such as multiple sclerosis (MS) or rheumatoid arthritis (RA). The analogue comprises a peptide with an amino acid substitution at amino acid position 14 of the wild-type (WT) peptide sequence (or a position corresponding to position 14 of the WT peptide sequence). The analogue exhibits selectivity for Kv1.3 over Kv1.1 and other potassium channels relative to the WT peptide.

19 Claims, 5 Drawing Sheets

SCORPION TOXIN ANALOGUE AND METHOD FOR TREATING AUTOIMMUNE DISEASES

CROSS REFERENCE TO RELATED APPLICATIONS

This application is a national stage application under 35 U.S.C. 371 and claims the benefit of PCT Application No. PCT/AU2013/001249 having an international filing date of 28 Oct. 2013, which designated the United States, the disclosure of which is incorporated herein by reference.

TECHNICAL FIELD

The present invention relates to a novel peptide analogue of the *Heterometrus spinnifer* toxin HsTX1, and its application as, for example, a therapeutic agent for treating an autoimmune disease.

BACKGROUND

The voltage-gated potassium channel Kv1.3 is significantly up-regulated in activated effector memory ($T_{EM}$) cells in humans (Wulff H et al., 2003; Beeton C et al., 2006). As a consequence, Kv1.3 blockers constitute valuable new therapeutic leads for the treatment of autoimmune diseases mediated by $T_{EM}$ cells, such as multiple sclerosis (MS) and rheumatoid arthritis (RA) (Beeton C et al., 2011; Chi V et al., 2012).

Figure 1:
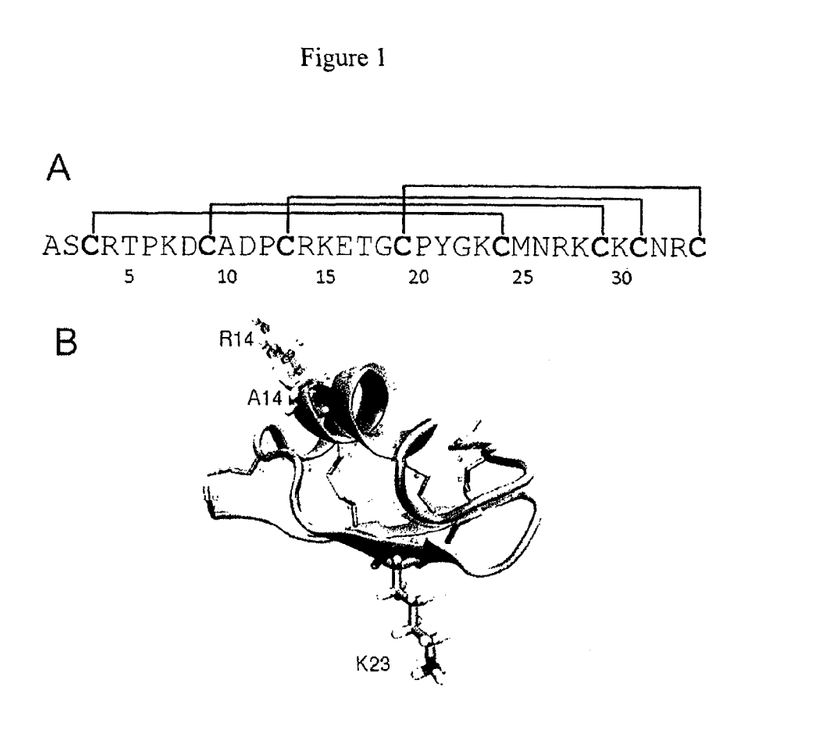
FIG. 1 provides (A) the amino acid sequence of HsTX1 (SEQ ID NO: 1) showing the positions of the four disulphide bridges, and (B) a simulated structure of HxTX1[R14A] (dark grey) superposed on the solution structure of HsTX1 (Savarin P et al., 1999) (transparent grey) to show that the R14A mutation does not cause any structural changes. Both structures are obtained from equilibrated MD simulations. The side chains of residue 14 and Lys23 in both structures are shown.

HsTX1 toxin is a 34-residue, C-terminally amidated peptide from the scorpion *Heterometrus spinnifer*, which is cross-linked by four disulphide bridges (Lebrun B et al., 1997). Its amino acid sequence (SEQ ID NO: 1) and the locations of the four disulphide bridges are shown in FIG. 1. The solution structures of the synthetic toxin (Savarin P et al., 1999) and a chimaera consisting of the N-terminal half of the closely-related scorpion toxin maurotoxin (MTX) and the C-terminal half of HsTX1 (Regaya I et al., 2004) were found to be very similar to the canonical fold adopted by related scorpion toxins that contain only three disulphides, which consists of an N-terminal helix structure connected to a C-terminal two-stranded antiparallel β-sheet.

HsTX1 is a potent blocker of potassium channels. For example, it has been found that the peptide inhibited rat Kv1.3 channels with an $IC_{50}$ of ca 12 pM and that it did not compete with $^{125}$I-apamin for binding to rat brain synaptosomal membranes (Lebrun B et al., 1997), although it did compete efficiently with $^{125}$I-kaliotoxin for binding to voltage-gated K$^+$ channels on the same preparation ($IC_{50}$ ca 1 pM). It is thus, a more potent Kv1.3 channel blocker than MTX and far more specific (Lebrun B et al., 1997). Subsequent studies have confirmed the marked preference of HsTX1 for Kv1.3 over Kv1.1, Kv1.2 and $K_{Ca}3.1$ channels (Regaya I et al., 2004). This high selectivity for Kv1.3 makes HsTX1 a potentially attractive candidate for the treatment of autoimmune diseases, as it has been shown that blockade of this channel in self-reactive $T_{EM}$ cells is effective in preventing the tissue damage associated with these conditions (Wulff H et al., 2003; Beeton C et al., 2006; Beeton C et al., 2011). Indeed, a considerable effort has been devoted to developing Kv1.3-selective analogues of the sea anemone peptide ShK (designated ShK-K-amide) as therapeutics for multiple sclerosis (Chi V et al., 2012; Pennington M W et al., 2012; Pennington M W et al., 2009) and one of these analogues has recently entered phase 1 clinical trials.

In an effort to understand the molecular basis for the potency and selectivity of HsTX1 for Kv1.3, the present applicants recently undertook a computational study of its interaction with Kv1.1, 1.2 and 1.3. Accurate models of Kv1x.-HsTx1 complexes were created using docking and molecular dynamics simulations. For each complex, the binding free energy of HsTx1 was determined from the potential of mean force calculations, with good agreement being found between the computed and experimental binding free energies. Comparison of the binding modes of HsTx1 with Kv1.1 and Kv1.3 revealed that the lower affinity of HsTx1 for Kv1.1 is due to its inability to come close to the pore domain of the channel, which prevents the pore-inserting lysine residue from making proper contacts with the tyrosine carbonyls in the "selectivity filter" of the channel.

In work leading to the present invention, the present applicants utilised the abovementioned models to design an analogue of HsTX1, namely HxTX1[R14A], with even greater selectivity for Kv1.3 over Kv1.1 and other channels. While not wishing to be bound by theory, it was predicted that the R14A mutation would perturb the binding mode of HsTX1. However, since the change in binding free energy associated with this mutation may not be reliably calculated using path-independent methods such as free energy perturbation, another approach using umbrella sampling molecular dynamics (MD) simulations was performed to determine the binding free energies of the peptide and its analogue from potential of mean force (PMF) calculations. This PMF method predicted that the R14A mutation in HsTX1 will yield >2 kcal/mol gain for the Kv1.3/Kv1.1 selectivity free energy relative to the wild-type (WT) peptide. Functional assays have subsequently confirmed the predicted selectivity gain for HsTX1[R14A] and thereby indicate that this analogue may be suitable for the development of a therapeutic agent and method for the treatment of autoimmune diseases.

SUMMARY

According to a first aspect, the present invention provides an analogue of *Heterometrus spinnifer* toxin HsTX1 comprising a peptide including an amino acid substitution (eg an R→X substitution) at amino acid position 14 (or a position corresponding to position 14 of the amino acid sequence shown as SEQ ID NO: 1).

Preferably, the amino acid substitution at position 14 (or a position corresponding to position 14 of the amino acid sequence shown as SEQ ID NO: 1) is selected from the group consisting of an arginine (R) to alanine (A) substitution (ie an R→A substitution), an arginine (R) to valine (V) substitution (ie an R→V substitution), an arginine (R) to phenylalanine (F) substitution (ie an R→F substitution), and an arginine (R) to 2-aminobutyric acid (Abu) substitution (ie an R→Abu substitution).

Preferably, the analogue is a peptide comprising or consisting of the following amino acid sequence:

ASCRTPKDCADPCAKETGCPYGKCMNRKCKC-NRC (SEQ ID NO: 2).

The analogue of the present invention may be suitable for the development of a therapeutic method for the treatment of autoimmune diseases and/or inhibiting T lymphocyte proliferation.

Thus, in a second aspect, the present invention provides a method of inhibiting T lymphocyte proliferation in a subject, said method comprising administering to the subject an effective amount of the analogue of the first aspect, optionally in combination with a pharmaceutically acceptable carrier.

Further, in a third aspect, the present invention provides a method of treating an autoimmune disease in a subject, said method comprising administering to the subject an effective amount of the analogue of the first aspect, optionally in combination with a pharmaceutically acceptable carrier.

Preferably, the autoimmune disease treated in accordance with the method of the third aspect, is an autoimmune disease mediated by $T_{EM}$ cells such as multiple sclerosis (MS) and rheumatoid arthritis (RA).

DETAILED DESCRIPTION

The amino acid sequence of native or "wild-type" (WT) HsTx1 is as follows:

(SEQ ID NO: 1)
ASCRTPKDCADPCRKETGCPYGKCMNRKCKCNRC;

with an amidated C-terminal.

The structure of WT HsTx1 is shown in FIG. 1 and consists of an α helix sitting on a β sheet with two strands. This structure is stabilised by four disulphide bridges between Cys3-Cys24, Cys9-Cys29, Cys13-Cys31 and Cys19-Cys34. The first three of these are similar to other scorpion toxins with three disulphide bridges and are responsible for the common α/β scaffold motif (Mouhat S et al., 2004). The fourth disulphide bridge has been shown to keep the β sheet structure in a twisted configuration (Carrega L et al., 2005). Its removal changes the β sheet to a non-twisted configuration and this has a substantial effect on its affinity for Kv1.3, reducing it by fifty-fold (Carrega L et al., 2005). Thus, the β sheet structure of HsTx1 is important for its high-affinity binding to Kv1.3. This can be appreciated from FIG. 1, where HsTx1 is presented with the pore-inserting lysine (K23) pointing downward; as mentioned above, this residue interacts with tyrosine carbonyls within the potassium channel effectively acting as a "selectivity filter".

As it is considered that relative selectivity for Kv1.3 over Kv1.1 is an important criterion for potential therapeutic agents for the treatment of autoimmune disease in humans (Beeton C et al., 2011; Chi V et al., 2012), the present applicants investigated the possibility of modifying the HsTX1 peptide, at a site distant from the K23 residue, to determine whether improvements in the binding to one channel versus the other, could be achieved. Through computational modelling and docking, it has been shown that modification at residue 14 is able to impart selectivity for the Kv1.3 channel versus the Kv1.1 channel.

Thus, in a first aspect, the present invention provides an analogue of *Heterometrus spinnifer* toxin HsTX1 comprising a peptide including an amino acid substitution at amino acid position 14 (or a position corresponding to position 14 of the amino acid sequence shown as SEQ ID NO: 1).

The amino acid substitution at position 14 (or a position corresponding to position 14 of the amino acid sequence shown as SEQ ID NO: 1) may be an R→X substitution, wherein X is any suitable amino acid, but preferably one selected from the twenty (20) standard amino acids encoded by genetic code. X may, however, be a non-standard amino acid such as, for example, certain Nα-alkylamino acids (eg N-methyl glycine (sarcosine) and N-methyl alanine), other amino acids such as 2-aminobutyric acid (Abu), amino isobutyric acid, 3-aminoadipic acid (Aad), ornithine, citrulline, amino-oxyserine, homo-arginine, aminosuberic acid and β-2- and β-3-napthylalanine, ring-substituted phenylalanine (Phe) analogues (eg 2,3,4,5,6-pentafluoro-phenylalanine, 4-chloro-phenylalanine, methyl-phenylalanine and phosphono-phenylalanine), phospho-tyrosine (pTyr), selenocysteine and selenomethionine.

Preferably, the amino acid substitution at position 14 (or a position corresponding to position 14 of the amino acid sequence shown as SEQ ID NO: 1) is selected from the group consisting of an arginine (R) to alanine (A) substitution (ie an R→A substitution), an arginine (R) to valine (V) substitution (ie an R→V substitution), an arginine (R) to phenylalanine (F) substitution (ie an R→F substitution), and an arginine (R) to 2-aminobutyric acid (Abu) substitution (ie an R→Abu substitution).

Preferably, the analogue is provided in an isolated form.

Preferably, the analogue is a peptide comprising one of the following amino acid sequences:

```
                                           (SEQ ID NO: 2)
ASCRTPKDCADPCAKETGCPYGKCMNRKCKCNRC;

(SEQ ID NO: 3)
ASCRTPKDCADPCVKETGCPYGKCMNRKCKCNRC;

(SEQ ID NO: 4)
ASCRTPKDCADPCFKETGCPYGKCMNRKCKCNRC;
and (SEQ ID NO: 5)
ASCRTPKDCADPCXKETGCPYGKCMNRKCKCNRC,
``` where X is 2-aminobutyric acid (Abu).

However, it will be understood by those skilled in the art that the analogue may also be a peptide that comprises a variant amino acid sequence of SEQ ID NO: 1 that not only includes a position 14 amino acid substitution, but also one or more other minor variations which, preferably, do not substantially alter the function of the peptide (eg despite the additional variation(s), the peptide maintains the ability of binding to and blocking the activation the potassium channel Kv1.3). Such variation(s) may include one or more conservative amino acid substitutions such as: G, A, V, I, L, M; D, E; N, Q; S, T; K, R, H; F, Y, W, H; and P, Nα-alkylamino acids. Other substitutions may include the substitution of one or more L-amino acid(s) with a D-amino acid(s). Other amino acid variations that may be present include one or more amino acid deletion or addition (eg insertion). One example of a particular amino acid addition is the addition of a methionine (M) residue to the N-terminal of the analogue, as may be a consequence of production of the peptide by recombinant techniques.

Other additions that may be made to, for example, the N-terminal or C-terminal sequence may comprise short amino acid sequences (eg 2 to 10 amino acids in length) or long amino acid sequences (eg 11 or more amino acids) which confer various additional functionalities or properties, such as improved bioavailability, protein recovery or expression (eg a fusion partner); although, typically, a peptide provided with an additional amino acid sequence will have a total length of not more than about 50 amino acids.

It will be understood that one or more amino acid deletion or addition may affect the amino acid residue numbering of the peptide (most significantly residue 14), however those skilled in the art will be able to readily recognise the amino acid positions corresponding to those of the amino acid sequence shown as SEQ ID NO: 1; for example, where the analogue includes a methionine (M) residue addition to the N-terminal, the amino acid position corresponding to R14 of the amino acid sequence shown as SEQ ID NO: 1 will, of course, be amino acid position 15. Similarly, where the analogue includes an additional short sequence of, for example, five (5) amino acids at the N-terminal, the amino acid position corresponding to R14 of the amino acid sequence shown as SEQ ID NO: 1 will be amino acid position 19.

Notwithstanding the above, the analogue of the present invention may additionally or alternatively, comprise amino acid sequences that have been modified either by natural processes, such as post-translational processing, or by chemical modification techniques such as those well known to those skilled in the art (eg Pegylation). Such modifications can occur anywhere in the analogue, including within the peptide backbone, the amino acid side-chains and/or the N- and/or C-termini. It will also be appreciated that the same types of modifications may be present in the same or at varying degrees at several sites in the functional fragments. Moreover, other modifications that may be present in the analogue include the addition of an N-terminal spacer/linker moiety such as β-alanine, 8-amino-3,6-dioxaoctanoic acid ("mini-PEG™") and 11-amino-3,6,9-trioxaundecanoic acid ("mini-PEG3™") for attaching, for example, a biochemical tag or chelator such as Fluorescein isothiocyanate (5-FITC), 5-carboxyfluorecein (5-Fam), 5-(and-6)-Carboxytetramethylrhodamine] (5,6-TAMRA), an Alexa Fluor® dye (Life Technologies Corporation, Carlsbad, Calif., United States of America), a cyanine dye, near-IR dye, 1,4,7,10-tetraazacyclododecane-1,4,7,10-tetraacetic acid (DOTA), 2-(4,7-bis(2-(tert-butoxy)-2-oxoethyl)-1,4,7-triazonan-1-yl)acetic acid (NOTA), diethylene triamine pentaacetic acid (DPTA) etc.

One preferred example of chemical modification is C-terminal amidation. As mentioned above, WT HsTX1 has an amidated C-terminal, which has been found to confer five-fold greater affinity for Kv1.3 compared to a synthetic carboxylated form of the toxin peptide. It is anticipated that C-terminal amidation of the analogue of the present invention will similarly show greater affinity for the Kv1.3 channel (ie relative to a carboxylated form thereof). Accordingly, the analogue of the present invention may preferably have an amidated C-terminal. Methods for the amidation of the C-terminal of a peptide (eg α-amidation) are well known to those skilled in the art, including, for example, the methodologies described by Kim K-H et al. (Kim K-H et al., 2001).

Preferably, the analogue is a peptide that shows the same pattern of disulphide bridging as WT HsX1 (ie Cys3-Cys24, Cys9-Cys29, Cys13-Cys31 and Cys19-Cys34) or otherwise has four disulphide bridges between cysteine residues at positions corresponding to 3/24, 9/29, 13/31 and 19/34 of the amino acid sequence shown as SEQ ID NO: 1). As such, where the analogue is a peptide comprises a variant amino acid sequence of SEQ ID NO: 1 (ie an amino acid sequence of SEQ ID NO: 1 that not only includes a position 14 amino acid substitution, but also one or more other minor variations as described above), it is to be understood that, preferably, the analogue shows the same pattern of disulphide bridging as WT HsX1 (or otherwise has four disulphide bridges between cysteine residues at positions corresponding to 3/24, 9/29, 13/31 and 19/34 of the amino acid sequence shown as SEQ ID NO: 1) notwithstanding the presence of variation(s) within the amino acid sequence. Moreover, such an analogue also preferably shows a μ sheet in substantially the same twisted configuration as that of WT HsTX1.

Preferably, the analogue is a peptide consisting of one of the amino acid sequences shown as SEQ ID NOS: 2-5.

Most preferably, the analogue is a peptide consisting of the amino acid sequence shown as SEQ ID NO: 2; referred to herein as the peptide analogue, HsTX1[R14A]. Preferably, HsTX1[R14A] is provided in a C-terminal amidated form.

The analogue of the present invention may be produced using synthetic or recombinant techniques well known to those skilled in the art.

It has been found that amino acid substitution at amino acid position 14 (or a position corresponding to position 14 of the amino acid sequence shown as SEQ ID NO: 1) causes destabilisation of HsTX1 binding to Kv1.1 (thereby improving its relative selectivity to Kv1.3). In the computational modelling and docking, this was reflected in an increase in the Kv1.3/Kv1.1 selectivity free energy from 3.9 kcal/mol in HsTX1 to 6.2 kcal/mol in HsTX1[R14A]. While not wishing to be bound by theory, it is considered that this is sufficient to render the HsTX1 analogue effectively inactive on the Kv1.1 channel.

It is known to those skilled in the art that Kv1.3 channel blockers are potent inhibitors of the proliferation of T lymphocytes. It is also known that Kv1.3 channel blockers offer considerable promise for the treatment of autoimmune diseases mediated by $T_{EM}$ cells, such as multiple sclerosis (MS) and rheumatoid arthritis (RA). Accordingly, the analogue of the present invention may be suitable for the development of a therapeutic method for the treatment of autoimmune diseases and/or inhibiting T lymphocyte proliferation.

Thus, in a second aspect, the present invention provides a method of inhibiting T lymphocyte proliferation in a subject, said method, comprising administering to the subject an effective amount of the analogue of the first aspect, optionally in combination with a pharmaceutically acceptable carrier.

Further, in a third aspect, the present invention provides a method of treating an autoimmune disease in a subject, said method comprising administering to the subject an effective amount of the analogue of the first aspect, optionally in combination with a pharmaceutically acceptable carrier.

The autoimmune disease to be treated in accordance with the method of the third aspect is preferably an autoimmune disease mediated by $T_{EM}$ cells such as, for example, MS and RA.

The subject to be treated will typically be a human. However, the invention is also applicable to non-human subjects such as, for example, livestock (eg calves, lambs and foals), exotic animals (eg tiger and lion cubs and elephant calves and the like) and companion animals (such as puppies and kittens).

The analogue is preferably administered, adapted and/or formulated in a manner or medicament ensuring that, upon administration to the subject, an effective amount of said agent is delivered to the subject. As such, the analogue may be, for example, formulated into any suitable medicament; such as a pharmaceutical composition for oral, buccal, nasal, subcutaneous, intramuscular, inhalative and intravenous administration. Typically, such a pharmaceutical composition will be administered to the subject in an amount which is effective to achieve a therapeutic effect, and may therefore provide between about 0.01 and about 100 µg/kg body weight per day of the analogue, and more preferably, provide from 0.05 and 25 µg/kg body weight per day of the analogue. A suitable pharmaceutical composition may be intended for single daily administration, multiple daily administration, or controlled or sustained release, as needed to achieve the most effective result. However, notwithstanding the above, it will be understood by those skilled in the art that the administered amount of the analogue, and the frequency of administration for any particular subject, may vary and depend upon a variety of factors including the activity of the analogue, the metabolic stability and length of action of the analogue, the age, body weight, sex, health, mode and time of administration, rate of excretion of the analogue, and the severity of the autoimmune disease to be treated. A suitable pharmaceutical composition may be formulated for inhalative administration (such as in the form of an aerosol), oral administration (such as in the form of a tablet, capsule, granules or powders), nasal administration (eg such as in the form of a spray or inhalable powder) or parenteral administration (such as by subcutaneous, intravenous or intramuscular injection or infusion).

In a fourth aspect, the present invention provides the use of the analogue of the first aspect in the treatment of an autoimmune disease, preferably an autoimmune disease mediated by $T_{EM}$ cells such as MS and RA.

Moreover, in a fifth aspect, the present invention provides the use of the analogue of the first aspect in the preparation of a medicament for treating an autoimmune disease, preferably an autoimmune disease mediated by $T_{EM}$ cells such as MS and RA.

As mentioned above, the analogue of the present invention may be produced using recombinant techniques well known to those skilled in the art. Accordingly, in a further aspect of the present invention, the invention provides a polynucleotide molecule (preferably, in an isolated form) comprising a nucleotide sequence encoding the analogue of the first aspect and, preferably, one comprising or consisting of the amino acid sequence shown as SEQ ID NO: 2. In a still further aspect, the present invention provides a cloning or expression vector comprising such a polynucleotide molecule. Moreover, in yet a still further aspect, the present invention provides a host cell (eg a prokaryotic or eukaryotic cell) including the polynucleotide or cloning or expression vector, wherein said host cell is capable, for example, of expressing the analogue in culture.

The present invention is hereinafter further described by way of the following non-limiting examples and accompanying figures.

EXAMPLE 1

Design and Evaluation of a Scorpion Toxin HsTX1 Analogue

Materials and Methods

Peptide Synthesis—HsTX1 was synthesised on a Prelude peptide synthesiser using an Fmoc-tBu strategy. The peptide was synthesised starting with Rink amide resin (Peptides International, Louisville, Ky., United States of America). Prior to coupling the Arg at position 14, the resin was split into equal portions replaced into separate reaction vessels and coupled with either Arg, Ala, Val, Phe or Abu. The remainder of the sequence was subsequently continued until the full-length peptide was assembled. All couplings were mediated with diisopropyl carbodiimide and 6-chloro-hydroxybenzotriazole. Following solid-phase assembly of the linear peptide chain, the peptide was cleaved from the solid support and simultaneously deprotected using Reagent K for 2 hours at room temperature. The crude peptide was then precipitated into ice cold diethyl ether and washed thoroughly to remove cationic scavengers from the cleavage cocktail, dissolved in 50% aqueous acetic acid, then diluted in water and the pH adjusted to 8.0 with $NH_4OH$. Disulphide bond formation was facilitated with reduced and oxidised glutathione according to previously used protocols for ShK (Pennington M W et al., 1996). The progress of folding was followed by RP-HPLC using a Phenomenex Luna C18 column (Phenomenex Inc., Torrance, Calif., United States of America) using a gradient of acetonitrile versus $H_2O$ containing 0.05% TFA from 10-70% over 35 min. Folding of the four disulphide bonds was also confirmed by the loss of 8 mass units from the crude material as determined by ESI-MS. The correctly folded peptides were then purified by preparative RP-HPLC using a Phenomenex Luna C18 column with a linear gradient of acetonitrile versus $H_2O$ buffered with 0.05% TFA. Fractions with a purity of greater than 95% were pooled and lyophilised. The final products were characterised by analytical HPLC, electrospray ionisation mass spectroscopy (ESI-MS) and amino acid compositional analysis (AAA). The sea anemone peptide analogue ShK-K-amide was synthesised as previously described by Pennington M W et al. (Pennington M W et al., 2012).

NMR Spectroscopy—Samples were prepared by dissolving freeze-dried HsTX1 and HsTX1[R14A] in 90% $H_2O$/10% $^2H_2O$, pH 4.0, to concentrations of 500 and 400 µM, respectively. One-dimensional $^1H$ spectra and two dimensional homonuclear TOCSY spectra with a spin lock time of 70 ms were acquired at 35° C. on a Bruker Avance 600 MHz spectrometer (Bruker Corporation, Billerica, Mass., United States of America). A NOESY spectrum (mixing times 200 ms) was also acquired at 35° C. All spectra were processed in TOPSPIN (version 3.2, Bruker Biospin) and analysed using CcpNmr-Analysis (version 2.1.5). $^1H$ chemical shifts were referenced to the residual water signal. Chemical shift assignments for backbone and side chain protons of HsTX1 [R14A] were made by conventional analysis of TOCSY and NOESY spectra. A complete assignment of the proton NMR signals of HsTX1[R14A] was obtained.

CD Spectroscopy—HsTX1 and HsTX1[R14A] were dissolved in 10 mM acetate buffer at pH 3.8 and CD spectra were recorded on a Chirascan v4.2.12 spectropolarimeter at concentrations of 94 and 89 µM, respectively, at 20° C. Spectra were collected at 1 nm intervals over the wavelength range 260-190 nm in a 1 mm path-length cuvette.

Modelling and Docking—The structure of HsTX1[R14A] was generated from that of HsTX1 using the mutator plugin in the VMD software (Humphrey, W et al., 1996). For the Kv1.1 and Kv1.3 structures, previously described homology models (Rashid M H et al., 2012) were used. Initial poses for Kv1.x-ShK-K-amide complexes were found using the docking program HADDOCK (Dominguez C et al., 2003), and then refined in MD simulations. The most stable complex in each, case was further run for 20 ns to check equilibration and for data analysis. MD simulations were performed using the NAMD program (Phillips J C et al., 2005) with the CHARMM22 force field (MacKerell A D et al., 1998) including the CMAP correction (MacKerell A D et al., 2004). The PMF of each toxin was determined from the umbrella sampling MD simulations using the weighted histogram analysis method (Rashid M H et al., 2012; Kumar S et al., 1992).

Cells and Cell Lines—L929 mouse fibroblast cells stably expressing mKv1.1 and mKv1.3 channels (Grissmer S et al., 1994) were maintained in DMEM medium (Invitrogen Corporation, Carlsbad, Calif., United States of America) supplemented with 100 IU/mL penicillin, 0.1 µg/mL streptomycin, 2 mM L-glutamine, 10% heat-inactivated foetal bovine serum, and 0.5 mg/mL G418 (EMD Chemicals, Gibbstown, N.J., United States of America).

Freshly prepared buffy coats were purchased from the Gulf Coast Regional Blood Center (Houston, Tex.). Mononuclear cells were isolated from the buffy coats using Histopaque-1077 gradients (Sigma Corporation, St Louis, Mo., United States of America) and used immediately.

Electrophysiological Analysis—Experiments were conducted at room temperature in the whole-cell configuration of the patch-clamp technique. A manual setup and an automated Port-a-patch setup (Nanion, North Brunswick, N.J., United States of America) were used in parallel, both linked to a HEKA EPC10USB amplifier. The patch pipettes or chips had a resistance of 2-4 MΩ when filled with an internal solution containing (in mM): 145 KF, 10 HEPES, 10 EGTA, and 2 $MgCl_2$, pH 7.2, 290 mOsm. The bath solution contained (in mM): 160 NaCl, 4.5 KCl, 2 $CaCl_2$, 1 $MgCl_2$, 10 HEPES, pH 7.2, 300 mOsm. Kv currents were elicited every 30 s by 200-ms depolarising pulses from a holding potential of −80 mV to 40 mV. $K_d$ values and Hill coefficients were determined by fitting the Hill equation to the reduction of peak current measured at 40 mV.

T Lymphocyte Proliferation Assays—Proliferation assays were conducted as described previously (Beeton C et al., 2005). Briefly, mononuclear cells ($10^5$/well) were plated into 96-well plates and pre-incubated with the peptide blockers for 30 min at 37° C. in RPMI medium (Invitrogen) supplemented with 100 IU/mL penicillin, 0.1 µg/mL streptomycin, 2 mM L-glutamine, 1 mM sodium pyruvate, 1% non-essential amino acids, 1% RPMI vitamins, 50 µM β-mercaptoethanol, and 1% heat-inactivated foetal bovine serum. T lymphocyte activation and proliferation was induced by the addition of 40 ng/mL anti-CD3 antibodies (Clone OKT3, eBioscience, San Diego, Calif., United States of America). Cells were cultured for 72 h at 37° C. 5% $CO_2$, and [$^3H$]-thymidine was added during the last 16-18 h of culture. Cells were lysed by freezing at −20° C. After thawing, DNA was harvested onto fibreglass filters using a cell harvester (Inotech Biosystems International, Rockville, Md., United States of America). [$^3H$]-thymidine incorporation into the DNA of proliferating cells was measured using a β-scintillation counter (Beckman Coulter, Brea, Calif., United States of America).

Results and Discussion

Peptide Synthesis—The desire to modify HsTX1 at a site distant from Lys23 led to the use of docking simulations with both Kv1.1 and Kv1.3 to identify residues that would improve binding to one channel versus the other. As a consequence, Arg14 of the native HsTx1 sequence was substituted with one of Ala, Val, Phe or Abu, because Arg14 was predicted to impart selectivity for Kv1.3 versus Kv1.1. The peptides were assembled using standard Fmoc-tBu solid-phase peptide synthesis. The crude products were oxidised using the glutathione-mediated oxidative folding conditions that had been used successfully for analogues of the sea anemone peptide ShK. It was found that the R14-substituted HsTx1 analogues folded rapidly, resulting in the typical pattern of a major earlier-eluting peak by RP-HPLC followed by later-eluting misfolded species and side-products. Each HsTX1 analogue was purified to homogeneity by preparative RP-HPLC, and each was found to have the correct mass by ESI-MS, demonstrating that the four disulphide bonds had been formed. The yield was ~40% of theory based upon the starting resin.

Figure 2:
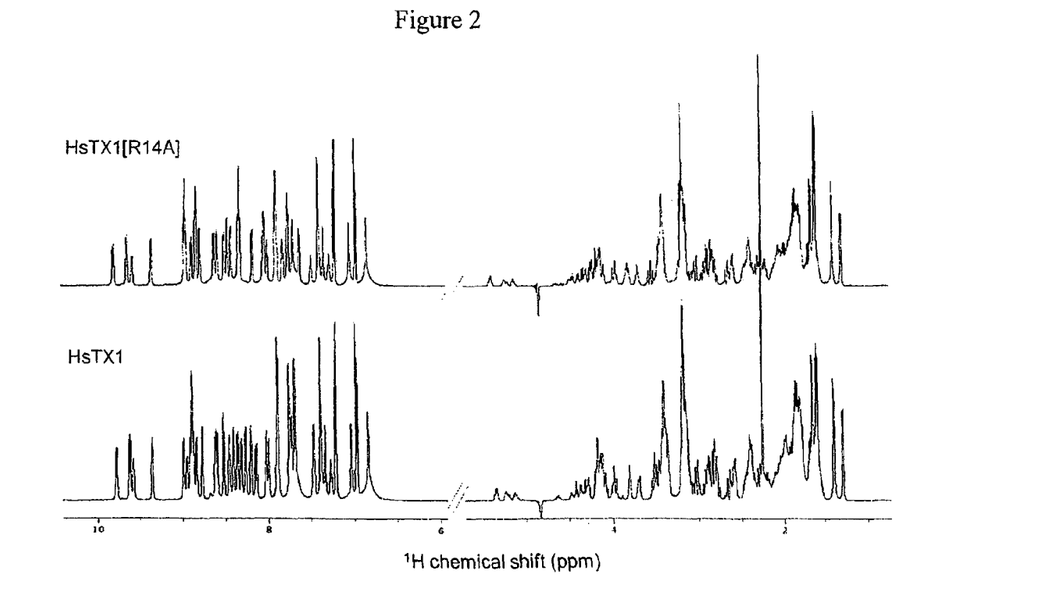
FIG. 2 provides a comparison of 1D $^1$H NMR spectra of wild-type (WT) HsTX1 (bottom) and HxTX1[R14A], both in water at pH 4.0, and acquired on a Bruker Avance 600 MHz spectrometer at 35° C. The amide-aromatic regions of both spectra are expanded 2.5-fold vertically relative to the aliphatic regions. The artifacts around 4.86 ppm are from the residual water resonance.

Peptide Conformation—CD spectra were acquired on both HsTX1 and HsTX1[R14A] in dilute acetate buffer. Both peptides exhibited minima at around 221 nm and maxima at around 195 nm, very similar to those reported by Lebrun et al. (Lebrun B et al., 1997) and indicative of a folded peptide containing both α-helical and β-sheet secondary structure. One-dimensional NMR spectra of HsTX1 [R14A] showed sharp and well-dispersed resonances similar to those of wild-type (WT) HsTX1 (FIG. 2), indicating that the R14A mutation did not cause any significant perturbation of the native structure. To further verify the structural similarity of WT HsTX1 and HsTX1[R14A], chemical shift differences from random coil values for backbone amide, $H^α$ and $H^β$ resonances were plotted. This showed that the patterns of chemical shift deviations from random coil for HsTX1[R14A] closely resemble those for WT HsTX1, confirming that the three-dimensional structures are basically the same; with the same pattern of disulphide bridging (ie Cys3-Cys24, Cys9-Cys29, Cys13-Cys31 and Cys19-Cys34). A comparison of the WT structure with the simulated structure of the analogue is shown in FIG. 1B.

Figure 3:
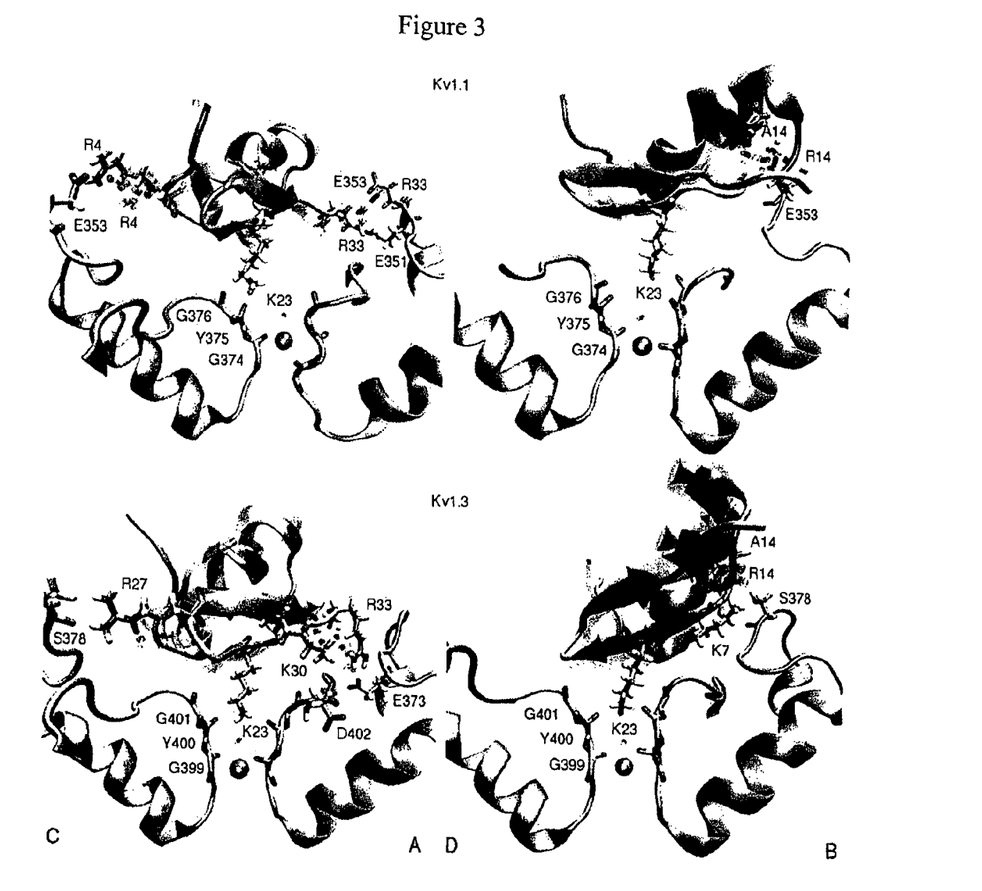
FIG. 3 provides a comparison of the binding modes of HxTX1[R14A] (dark grey) and HsTX1 (transparent grey) in complex with the Kv1.1 and Kv1.3 channels. Channel subunits are denoted C/D and A/B. The R14A mutation causes a small shift in the binding modes of the toxin in both complexes, resulting in some rearrangement of the contact pairs.
Figure 4:
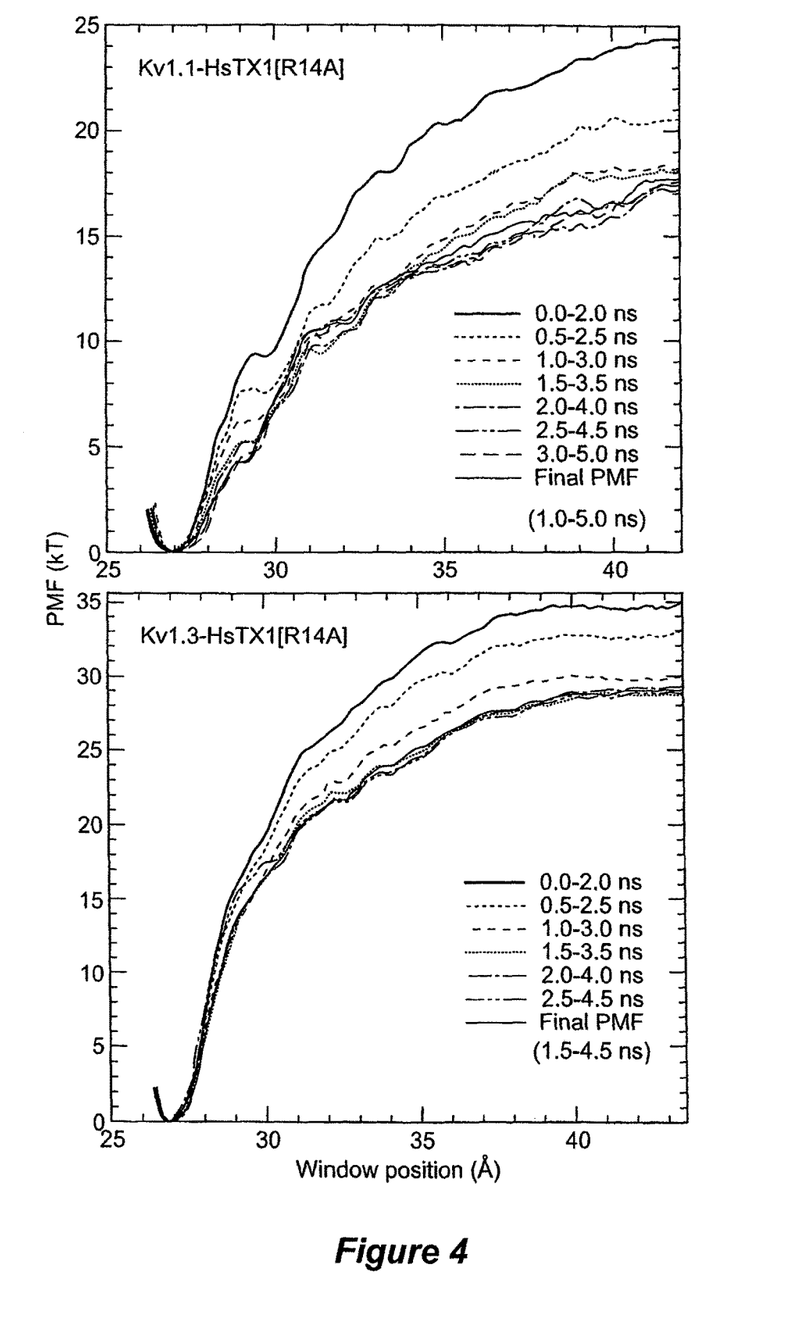
FIG. 4 provides graphs showing the convergence of the Kv1.x-HsTX1[R14A] PMFs from block data analysis. To reduce fluctuations, a large sampling size (2 ns) was used, which is slid in 0.5 ns steps over the range of the data. In Kv1.1, the PMFs converge quickly within 1 ns, after which they fluctuate around a base line. In Kv1.3, equilibration occurs around 1.5 ns.
Figure 5:
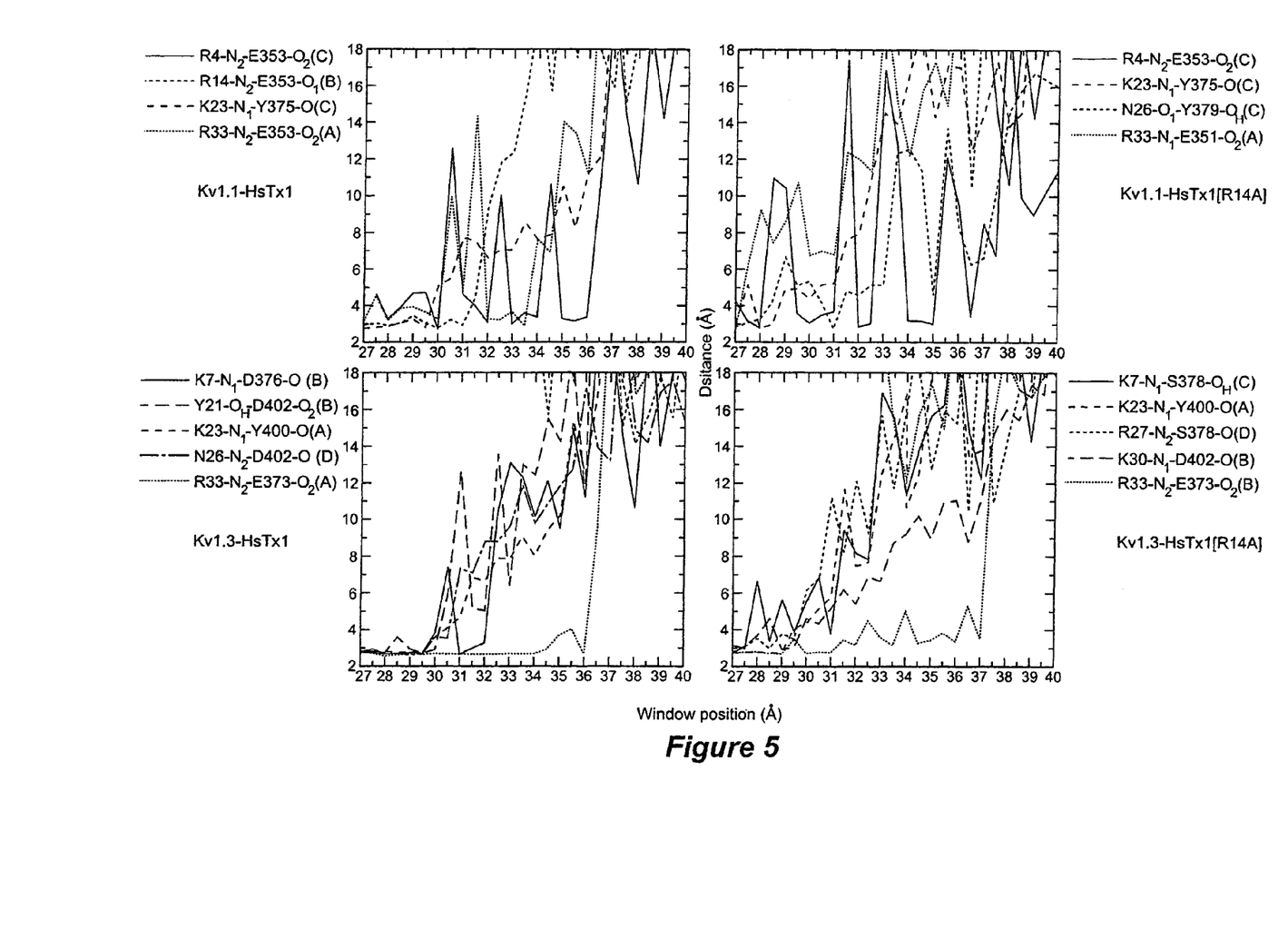
FIG. 5 provides graphs showing the average distance between the interacting pairs of Kv1.x-HsTx1 (left) and Kv1.x-HsTx1[R14A] (right) plotted as a function of the window position. All the important pairs identified in Table 1 herein are considered. The trajectory data are taken from the umbrella sampling simulations that were used in construction of the final PMFs.
Figure 6:
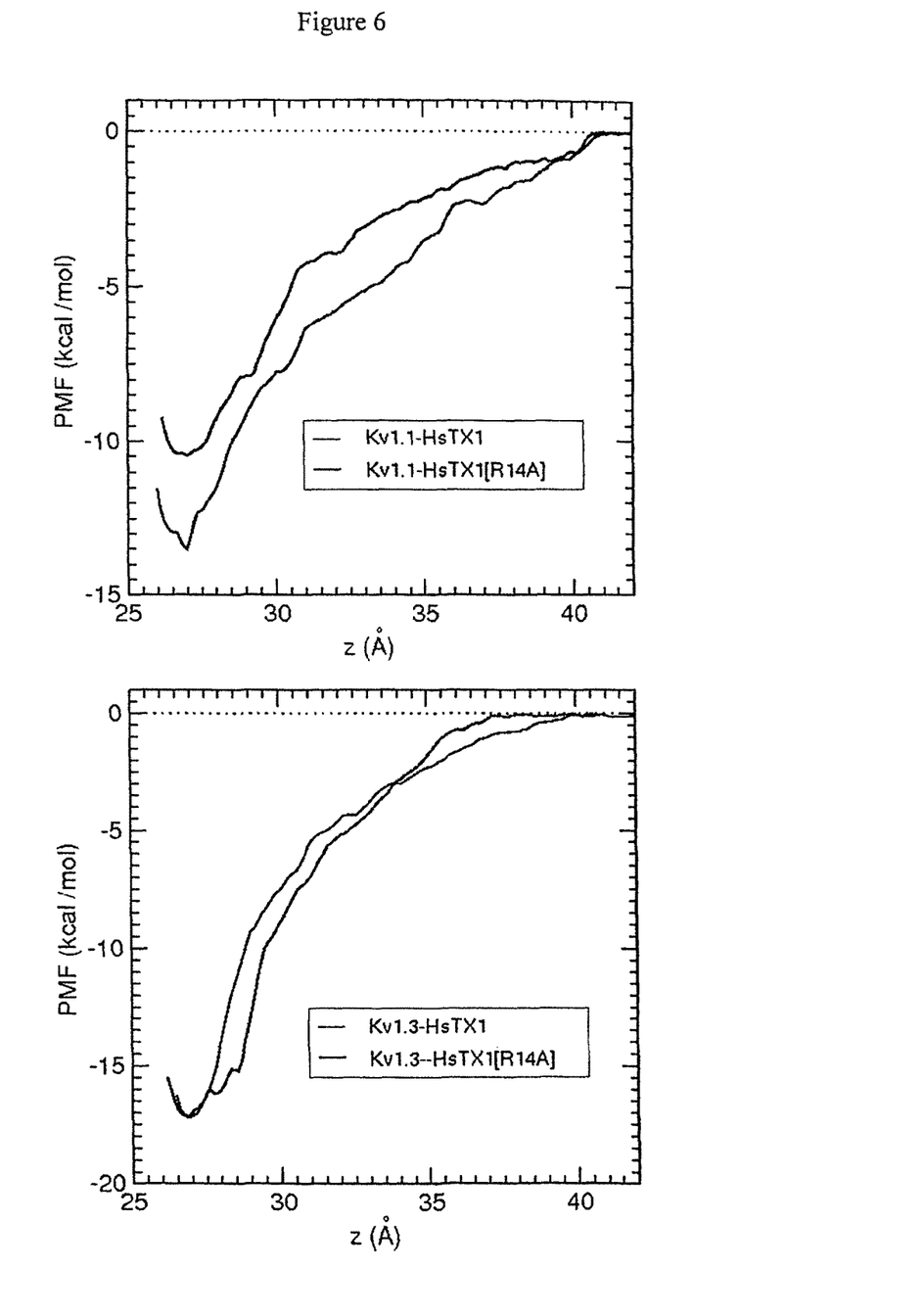
FIG. 6 provides graphs showing a comparison of the PMFs for the unbinding of HsTX1[R14A] and HsTX1 from Kv1.1 (top) and Kv1.3 (bottom). The R14A mutation has little effect on the binding of HsTX1 to Kv 1.3 but substantially reduces its affinity for Kv1.1.

Interactions of HsTX1[R14A] with Kv1.3 and Kv 1.1—Snapshots of the Kv1.xHsTX1[R14A] complexes are shown in FIG. 3. It was observed that, while there are no large rotations, the structure of HsTX1[R14A] is slightly shifted relative to HsTX1. The effects of these changes on the binding modes are quantified in Table 1, which lists the average pair distances for the strongly interacting residues. In Kv1.1, the lost R14 contact is replaced by the N26Y379 H-bond. In addition, R33 switches from E353 to E351, making a weaker contact. In Kv1.3, there are still five contacts but two of them (Y21 and N26) are replaced by R27 and K30. From the comparison of the binding modes, it is expected that the R14A mutation reduces the affinity of the toxin to Kv1.1 but not to Kv1.3, thus improving the Kv1.3/Kv1.1 selectivity margin further. To calculate by how much, PMFs were constructed for the Kv1.x-HsTX1[R14A] complexes. Umbrella sampling MD simulations were performed as previously described for the binding of toxin peptides to potassium channels (Pennington M W et al., 2012; Chen P C et al., 2011; Rashid M H et al., 2012). Inspection of the backbone RMSD values of HsTX1[R14A] in each umbrella window showed that they exhibit a similar behaviour to those of HsTX1 (Rashid M H et al., 2012). Namely, binding suppresses the RMSD values relative to the bulk, but they return to the bulk values after the toxin unbinds. Thus, no artificial deformation of the peptide occurs during the PMF calculations. Convergence of the PMFs is demonstrated in FIG. 4. For Kv1.3, the PMF profile of HsTX1[R14A] and its convergence characteristics are very similar to those of HsTX1 (see FIG. 5 in Rashid M H et al., 2012). Despite weaker binding of HsTX1[R14A] to Kv1.1 relative to HsTX1, its PMF converges much faster. To understand this feature, it is necessary to examine how the pair distances change as the toxin is pulled out of the channel. These are shown in FIG. 5 for both complexes. Comparison of the pair distances for Kv1.3HsTX1[R14A] with those of Kv1.3HsTX1 (FIG. 5) shows that the pair distances exhibit a very similar behaviour in both complexes. In contrast, there is a notable difference between the pair distances in the Kv1.1 complexes. The large fluctuations in the R4 and R33 pair distances seen in the unbinding of HsTX1 occurs only for the R4 pair distance in HsTX1[R14A] while R33 dissociates in the first step of pulling and never makes a contact again. The reduction in the side chain fluctuations is presumably responsible for the faster convergence of the Kv1.1HsTX1[R14A]. More importantly, the R14A mutation caused further destabilisation of the binding mode, leading to a rapid detachment of the R33 contact. While this is compensated to a degree by the formation of the N26-Y379 H-bond, it is expected that the overall effect of the R14A mutation on the binding free energy of the toxin on Kv1.1 is more than the 2 kcal/mol value associated with a typical loss of a charge contact. The PMFs for HsTX1[R14A] are compared to those of HsTX1 in FIG. 6, and the absolute binding free energies obtained from the integration of the PMFs are listed in Table 2. The PMFs for Kv1.3 have almost the same well depth, and the corresponding binding free energies are also very similar (Table 2). In contrast, the R14A mutation reduced the well depth in Kv1.1 by 3 kcal/mol and increased the binding free energy of the toxin by 2.7 kcal/mol. Both of these results are in line with the qualitative expectations derived from comparison of the binding modes, namely, that the R14A mutation should not affect the toxin's affinity to Kv1.3 much but should reduce its affinity for Kv1.1. In summary, the R14A mutation has increased the Kv1.3/Kv1.1 selectivity free energy from 3.9 kcal/mol in HsTX1 to 6.2 kcal/mol in HsTX1[R14A]. This is sufficient to render HsTX1[R14A] effectively inactive on Kv1.1.

TABLE 1

Comparison of the strongly interacting pair distances in the HsTX1-Kv1.x complexes with those in the HsTX1[R14A]-Kv1.x complexes

| HsTX1 | Kv1.1 | MD average | HsTX1[R14A] | Kv1.1 | MD average |
|---|---|---|---|---|---|
| $R4-N_2$ | $E353-O_2(C)$ | $3.0 \pm 0.5$ | $R4-N_2$ | $E353-O_2(C)$ | $2.7 \pm 0.3$ |
| $R14-N_2$ | $E353-O_1(B)$ | $2.9 \pm 0.3$ | | | |
| $K23-N_1$ | $Y375-O(C)$ | $2.7 \pm 0.3$ | $K23-N_1$ | $Y375-O(C)$ | $2.7 \pm 0.5$ |
| $K23-N_1$ | $G376-O(BC)$ | $3.0 \pm 0.2$ | $K23-N_1$ | $G376-O(BC)$ | $4.0 \pm 0.4$ |
| | | | $N26-O_1$ | $Y379-O_H(C)$ | $2.8 \pm 0.3$ |
| $R33-N_2$ | $E353-O_2(A)$ | $2.7 \pm 0.4$ | $R33-N_1$ | $E351-O_2(A)$ | $3.0 \pm 0.3$ |

| HsTX1 | Kv1.3 | MD average | HsTX1[R14A] | Kv1.3 | MD average |
|---|---|---|---|---|---|
| $T5-C_{\gamma2}$ | $M403-C\epsilon(C)$ | $3.7 \pm 0.3$ | | | |
| $K7-N_1$ | $S378-O(B)$ | $2.7 \pm 0.5$ | $K7-N_1$ | $S378-O(B)$ | $2.8 \pm 0.5$ |
| $Y21-O_H$ | $D402-O_2(B)$ | $2.7 \pm 0.2$ | | | |
| $K23-N_1$ | $Y400-O(ABC)$ | $2.7 \pm 0.3$ | $K23-N_1$ | $Y400-O(BCD)$ | $2.7 \pm 0.3$ |
| $N26-N_{\delta2}$ | $D402-O(D)$ | $2.8 \pm 0.4$ | | | |
| | | | $R27-N_2$ | $S378-O(C)$ | $2.7 \pm 0.4$ |
| | | | $K30-N_1$ | $D402-O(A)$ | $3.0 \pm 0.4$ |
| $R33-N_2$ | $E373-O_2(A)$ | $2.7 \pm 0.3$ | $R33-N2$ | $E373-O_2(A)$ | $2.8 \pm 0.3$ |

The average atom-atom distances obtained from the MD simulations are listed in columns 3 and 6 (in units of Å). Subscripts refer to the side chain atoms and the monomer identity is indicated in parentheses.

TABLE 2

Comparison of binding free energies for the HsTX1-Kv1.x and HsTX1[R14A]-Kv1.x complexes.

| Complex | $\Delta G_{well}$ | $G_b$ (PMF) | $G_b$ (exp) |
|---|---|---|---|
| Kv1.1-HsTX1 | −13.5 ± 0.3 | −10.1 ± 0.3 | −11.1 ± 0.1 |
| Kv1.1-HsTX1[R14A] | −10.5 ± 0.3 | −7.4 ± 0.3 | |
| Kv1.3-HsTX1 | −17.2 ± 0.3 | −14.0 ± 0.3 | −14.9 ± 0.2 |
| Kv1.3-HsTX1[R14A] | −17.1 ± 0.4 | −13.6 ± 0.4 | |

The relative binding free energies obtained from the well depth in the PMFs are shown in the second column. The standard binding free energies determined from the PMFs using eq 2 (third column) are compared to the experimental values in the last column. Errors in the binding free energies are estimated from the block data analysis of the PMF data. All energies are in kcal/mol.

Potency and Selectivity of Potassium Channel Blockade—Patch-clamp electrophysiology was used to determine the potency and selectivity of ShK and ShK-K-amide on Kv1.3 and Kv1.1 channels. As described previously (Kalman K et al., 1998; Chang S C et al., 2012), ShK inhibited Kv1.3 and Kv1.1 channels with similar potencies ($IC_{50}$ of 9±2 pM for Kv1.3 and 23±3 pM for Kv1.1). The ShK-K amide retained a high affinity for the Kv1.3 channels ($IC_{50}$ 26±3 pM), but displayed a much lower affinity for Kv1.1 channels ($IC_{50}$ 942±120 pM) resulting in a 36-fold selectivity for Kv1.3 over Kv1.1 channels. As a control for the contribution of the C-terminal amidation of ShK in this increase in selectivity of ShK-K-amide, the potency of ShK-amide on both channels was determined. It was found that the C-terminal amidation did not affect the selectivity of the peptide, with $IC_{50}$ values of 35±5 pM on Kv1.3 and 37±4 pM on Kv1.1 channels. However, the change in the relative affinity of ShK-K-amide indicated that a corresponding C-terminal modification of HsTX1 and/or substitution of the amino acid at position 14 of HsTX1 would similarly increase the potency of those peptides. This was subsequently confirmed using, as representative examples, the HsTX1[R14A] and HsTX1[R14Abu] analogues. That is, in a preliminary example, it was found that for HsTX1[R14A] at the high dose of 100 nM, there was a 10-16% current block (n=3) indicating that the $IC_{50}$ is well above 100 nM on Kv1.1 channels, while for HsTX1[R14Abu] at 100 nM, there was a 15-20% current block (n=3) also indicating that the $IC_{50}$ is well above 100 nM on Kv1.1 channels. These preliminary results clearly indicate that the R14-substituted HsTX1 analogues of the present invention show high levels of selectivity for Kv1.3 over Kv1.1 channels.

Inhibitory Effects on Human T Lymphocyte Proliferation—Kv1.3 channel blockers are potent inhibitors of the proliferation of human T lymphocytes. ShK-K-amide inhibited the proliferation of freshly-isolated human T cells with a similar potency ($IC_{50}$≈3 nM) to that of ShK and its well-characterised analogue ShK-186 (Wulff H et al., 2003; Beeton C et al., 2006; Chang S C et al., 2012; Tarcha E J et al., 2012). Given the selectivity of the HsTX1[R14A] and HsTX1[R14Abu] analogues described above, it is expected that the R14-substituted HsTX1 analogues of the present invention will demonstrate in equivalent experiments that, like ShK-K-amide, they are also potent inhibitors of the proliferation of human T lymphocytes.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

REFERENCES

Beeton C et al., *Mol Pharmacol* 67:1369-1381 (2005).
Beeton C et al., *Proc Natl Acad Sci USA* 103:17414-17419 (2006).
Beeton C et al., *Inflamm Allergy Drug Targets* 10:313-321 (2011).
Carrega Let al., *Proteins* 61:1010-1023 (2005).
Chang S C et al., *Toxicon* 60:840-850 (2012).
Chen P C et al., *Biophys J* 100:2466-2474 (2011).
Dominguez C et al., *J Am Chem Soc* 125:1731-1737 (2003).
Humphrey W et al., *J Mol Graph* 14:33-38 (1996).
Grissmer S et al., *Mol Pharmacol* 45:1227-1234 (1994).
Kalman K et al., *J Biol Chem* 273:32697-32707 (1998).
Kim K-H et al., *Biotechnol Bioprocess Eng* 6:244-251 (2001).
Kumar S et al., *J Comput Chem* 13:1011-1021 (1992).
Lebrun B et al., *Biochem J* 328 (Part 1):321-327 (1997).
MacKerell A D et al., *J Phys Chem B* 102:3586-3616 (1998).
MacKerell A D et al., *J Comput Chem* 25:1400-1415 (2004).
Mouhat S et al., *Biochem J* 378:717-726 (2004).
Pennington M W et al., *Biochemistry* 35:16407-16411 (1996).
Pennington M W et al., *Mol Pharmacol* 75:762-773 (2009).
Pennington M W et al., *FEBS Lett* 586:3996-4001 (2012).
Phillips J C et al., *J Comput Chem* 26:1781-1802 (2005).
Regaya I et al., *J Biol Chem* 279:55690-55696 (2004).
Savarin P et al., *Protein Sci* 8:2672-2685 (1999).
Tarcha E J et al., *J Pharmacol Exp Ther* 342:642-653 (2012).
Wulff H et al., *J Clin Invest* 111:1703-1713 (2003).

The invention claimed is:

1. A peptide analogue of *Heterometrus spinnifer* toxin HsTX1 comprising amino acid sequence SEQ ID NO:1, wherein the peptide analogue has an amino acid substitution corresponding to position 14 of SEQ ID NO:1 selected from the group consisting of an arginine (R) to phenylalanine (F) substitution, and an arginine (R) to 2-aminobutyric acid (Abu) substitution.

2. A method of inhibiting T lymphocyte proliferation in a subject, said method comprising administering to the subject an effective amount of a peptide analogue of *Heterometrus spinnifer* toxin HsTX1 comprising amino acid sequence SEQ ID NO:1, wherein the peptide analogue has an amino acid substitution corresponding to position 14 of SEQ ID NO:1, optionally in combination with a pharmaceutically acceptable carrier.

3. The method of claim 2, wherein the amino acid substitution corresponding to position 14 of SEQ ID NO:1 is selected from the group consisting of an arginine (R) to alanine (A) substitution (ie an R→A substitution), an arginine (R) to valine (V) substitution (ie an R→V substitution), an arginine (R) to phenylalanine (F) substitution (ie an R→F substitution), and an arginine (R) to 2-aminobutyric acid (Abu) substitution (ie an R→Abu substitution).

4. The method of claim 2, wherein the amino acid substitution corresponding to position 14 of SEQ ID NO:1 is an arginine (R) to alanine (A) substitution (ie an R→A substitution).

5. The method of claim 2, wherein the peptide analogue comprises an amino acid sequence selected from the group consisting of:

```
                                        (SEQ ID NO: 2)
ASCRTPKDCADPCAKETGCPYGKCMNRKCKCNRC;

(SEQ ID NO: 3)
ASCRTPKDCADPCVKETGCPYGKCMNRKCKCNRC;

(SEQ ID NO: 4)
ASCRTPKDCADPCFKETGCPYGKCMNRKCKCNRC;
and (SEQ ID NO: 5)
ASCRTPKDCADPCXKETGCPYGKCMNRKCKCNRC.
``` where X is 2-aminobutyric acid (Abu).

6. The method of claim 2, wherein the peptide analogue is a peptide that shows disulphide bridging between C3 and C24, C9 and C29, C13 and C31, and C19 and C34.

7. The method of claim 2, wherein the peptide analogue consists of the amino acid sequence SEQ ID NO: 2.

8. The method of claim 2, wherein the peptide analogue is in an isolated form.

9. The method of claim 2, wherein the peptide analogue further comprises an amidated C-terminus.

10. A method of treating an autoimmune disease in a subject, said method comprising administering to the subject an effective amount of a peptide analogue of *Heterometrus spinnifer* toxin HsTX1 comprising amino acid sequence SEQ ID NO:1, wherein the peptide analogue has an amino acid substitution corresponding to position 14 of SEQ ID NO:1, optionally in combination with a pharmaceutically acceptable carrier.

11. The method of claim 10, wherein the autoimmune disease to be treated is an autoimmune disease mediated by $T_{EM}$ cells.

12. The method of claim 10, wherein the autoimmune disease to be treated is multiple sclerosis (MS) or rheumatoid arthritis (RA).

13. The method of claim 10, wherein the amino acid substitution corresponding to position 14 of SEQ ID NO:1 is selected from the group consisting of an arginine (R) to alanine (A) substitution (ie an R→A substitution), an arginine (R) to valine (V) substitution (ie an R→V substitution), an arginine (R) to phenylalanine (F) substitution (ie an R→F substitution), and an arginine (R) to 2-aminobutyric acid (Abu) substitution (ie an R→Abu substitution).

14. The method of claim 10, wherein the amino acid substitution corresponding to position 14 of SEQ ID NO:1 is an arginine (R) to alanine (A) substitution (ie an R→A substitution).

15. The method of claim 10, wherein the peptide analogue comprises an amino acid sequence selected from the group consisting of:

```
                                        (SEQ ID NO: 2)
ASCRTPKDCADPCAKETGCPYGKCMNRKCKCNRC;

(SEQ ID NO: 3)
ASCRTPKDCADPCVKETGCPYGKCMNRKCKCNRC;
and (SEQ ID NO: 4)
ASCRTPKDCADPCFKETGCPYGKCMNRKCKCNRC;

(SEQ ID NO: 5)
ASCRTPKDCADPCXKETGCPYGKCMNRKCKCNRC,
``` where X is 2-aminobutyric acid (Abu).

16. The method of claim 10, wherein the peptide analogue is a peptide that shows disulphide bridging between C3 and C24, C9 and C29, C13 and C31, and C19 and C34.

17. The method of claim 10, wherein the peptide analogue consists of the amino acid sequence SEQ ID NO: 2.

18. The method of claim 10, wherein the peptide analogue is in an isolated form.

19. The method of claim 10, wherein the peptide analogue further comprises an amidated C-terminus.

* * * * *

SEQUENCE LISTING

```
<160> NUMBER OF SEQ ID NOS: 5

<210> SEQ ID NO 1
<211> LENGTH: 34
<212> TYPE: PRT
<213> ORGANISM: Heterometrus spinnifer

<400> SEQUENCE: 1
```

```
Ala Ser Cys Arg Thr Pro Lys Asp Cys Ala Asp Pro Cys Arg Lys Glu
1               5                   10                  15

Thr Gly Cys Pro Tyr Gly Lys Cys Met Asn Arg Lys Lys Cys Asn
            20                  25                  30

Arg Cys

<210> SEQ ID NO 2
<211> LENGTH: 34
<212> TYPE: PRT
<213> ORGANISM: Heterometrus spinnifer

<400> SEQUENCE: 2

Ala Ser Cys Arg Thr Pro Lys Asp Cys Ala Asp Pro Cys Ala Lys Glu
1               5                   10                  15

Thr Gly Cys Pro Tyr Gly Lys Cys Met Asn Arg Lys Lys Cys Asn
            20                  25                  30

Arg Cys

<210> SEQ ID NO 3
<211> LENGTH: 34
<212> TYPE: PRT
<213> ORGANISM: Heterometrus spinnifer

<400> SEQUENCE: 3

Ala Ser Cys Arg Thr Pro Lys Asp Cys Ala Asp Pro Cys Val Lys Glu
1               5                   10                  15

Thr Gly Cys Pro Tyr Gly Lys Cys Met Asn Arg Lys Lys Cys Asn
            20                  25                  30

Arg Cys

<210> SEQ ID NO 4
<211> LENGTH: 34
<212> TYPE: PRT
<213> ORGANISM: Heterometrus spinnifer

<400> SEQUENCE: 4

Ala Ser Cys Arg Thr Pro Lys Asp Cys Ala Asp Pro Cys Phe Lys Glu
1               5                   10                  15

Thr Gly Cys Pro Tyr Gly Lys Cys Met Asn Arg Lys Lys Cys Asn
            20                  25                  30

Arg Cys

<210> SEQ ID NO 5
<211> LENGTH: 34
<212> TYPE: PRT
<213> ORGANISM: Heterometrus spinnifer
<220> FEATURE:
<221> NAME/KEY: MISC_FEATURE
<222> LOCATION: (14)..(14)
<223> OTHER INFORMATION: X is 2-aminobutyric acid (Abu)

<400> SEQUENCE: 5

Ala Ser Cys Arg Thr Pro Lys Asp Cys Ala Asp Pro Cys Xaa Lys Glu
1               5                   10                  15

Thr Gly Cys Pro Tyr Gly Lys Cys Met Asn Arg Lys Lys Cys Asn
            20                  25                  30

Arg Cys
```